United States Patent [19]

Rizzo

[11] Patent Number: 4,865,613
[45] Date of Patent: Sep. 12, 1989

[54] LATERALLY OPERATIVE COSMETIC HAND

[76] Inventor: Mary B. Rizzo, 3967 Lytham Ct., Columbus, Ohio 43220

[21] Appl. No.: 215,311

[22] Filed: Jul. 5, 1988

[51] Int. Cl.$^4$ .............................................. A61F 2/54
[52] U.S. Cl. ........................................ 623/65; 623/57; 623/63; 623/64; 623/66
[58] Field of Search ........................ 623/57, 63, 64, 65, 623/66; 294/19.1, 86.4, 105, 106

[56] References Cited

U.S. PATENT DOCUMENTS

| | | | |
|---|---|---|---|
| 999,484 | 8/1911 | Carnes | 623/65 X |
| 1,042,413 | 10/1912 | Dorrance | 623/65 X |
| 1,819,317 | 8/1931 | Baehr | 623/65 |
| 2,701,370 | 2/1955 | Alderson | 623/66 X |
| 3,173,151 | 3/1965 | Glabiszewski | 623/64 |
| 4,159,545 | 7/1979 | Manning et al. | 623/65 |

FOREIGN PATENT DOCUMENTS

| | | | |
|---|---|---|---|
| 0309797 | 12/1918 | Fed. Rep. of Germany | 623/57 |
| 0315024 | 9/1919 | Fed. Rep. of Germany | 623/65 |
| 0101864 | 7/1917 | United Kingdom | 623/65 |
| 0113923 | 3/1918 | United Kingdom | 623/57 |

Primary Examiner—Richard J. Apley
Assistant Examiner—Joe H. Cheng
Attorney, Agent, or Firm—Watkins, Dunbar & Pollick

[57] ABSTRACT

The function and advantages of a split hook and a mechanical hand are combined into a single unit obviating the complex and difficult process of interchanging hook and hand units while at the same time providing the dexterity of a hook for grasping and manipulating small objects and the prehensile function of an operable locking thumb including extending holding times without the need for cable manipulation. Covering the split hook members with finger-shaped material and adding rigid fingers enhances the cosmetic appeal of the unit.

14 Claims, 2 Drawing Sheets

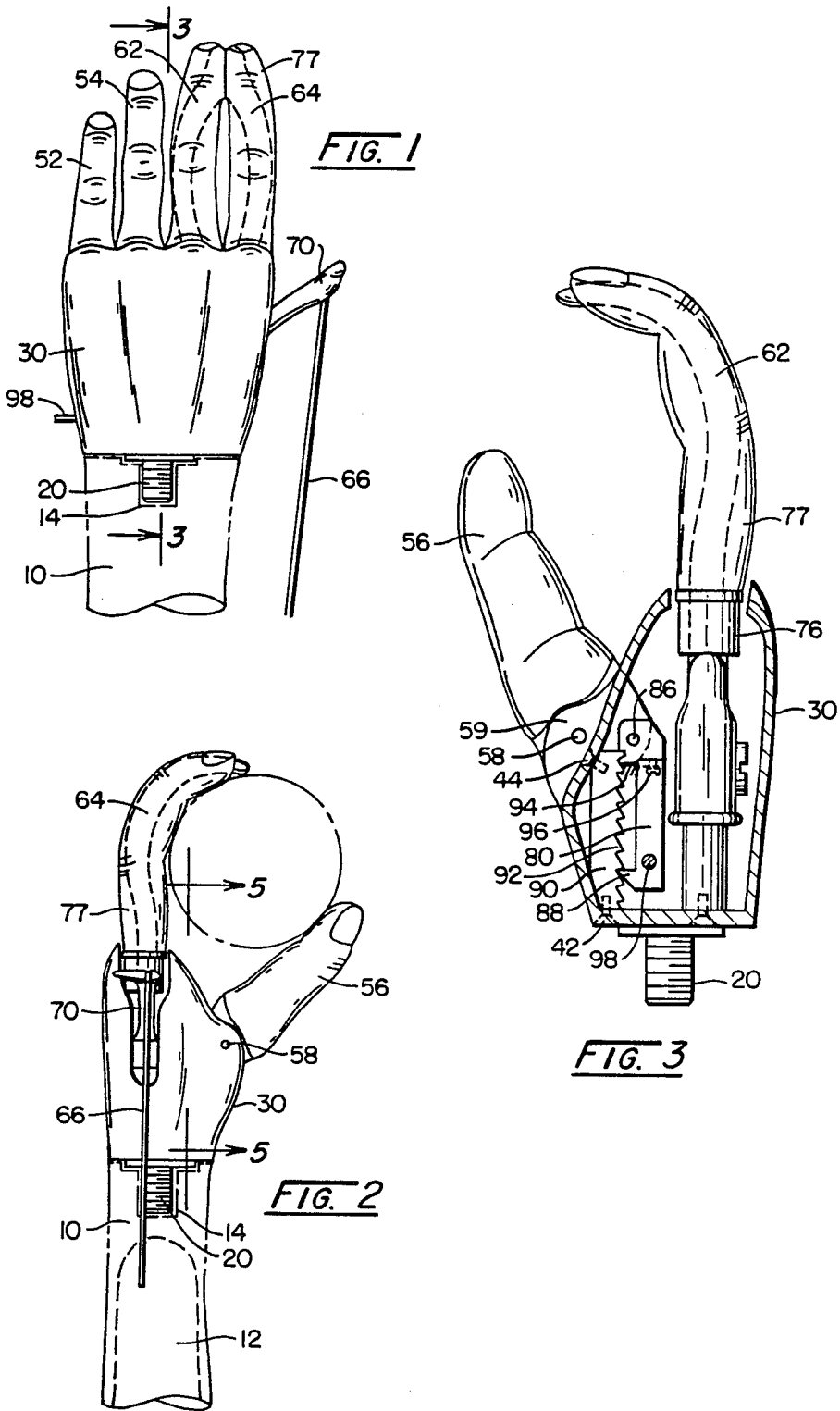

LATERALLY OPERATIVE COSMETIC HAND

FIELD OF INVENTION

The present invention relates to an improved hand prosthesis or artificial hand. More specifically, it combines the dexterity of a hook prosthesis with the prehensile function and cosmetic value of a mechanical hand.

BACKGROUND OF THE INVENTION

The traditional hook prosthesis has been the classic prosthesis for the amputee of a hand or forearm. Typically the hook or, more specifically, the split hook, consists of two hook sections joined at one end by a pivot. The terminal ends of the two sections are maintained in contact with each other by rubber bands wrapped around the two sections near the pivot point. A lever mounted on one of the hook sections and connected to a cable attached to the upper arm or shoulder is used to open the hook. The hook is typically lightweight, is capable of handling small objects, and provides maximum visibility. The hook is durable and provides a high pinch pressure while the force necessary to open it is relatively low. To its disadvantage, the hook is lacking in prehensile grip and natural appearance.

To overcome the lack of prehensile grip and poor cosmetic appearance of the hook, a hand prosthesis is often used, especially when the amputee is in public. In its simplest form the hand is merely a wooden, metal, or plastic model of a human hand. A basic improvement to this simple hand model has been the addition of controlled movement between the fingers and thumb of the hand resulting in prehensile grasp. In its basic form, the hand operates by a clamping action between the thumb and fingers. Typically, at least one finger is articulated and biased in opposition to an adjustable fixed thumb. U.S. Pat. Nos. 4,685,929 (Monestier), 4,685,924 (Massey), 4,291,421 (Massey). Generally the hand is much heavier than the hook, requires considerable more force than the hook to operate, and offers little in the precision necessary to handle small objects.

Because of the decided advantages and disadvantages of the hand and the hook, most arm amputees choose to purchase one of each. Although this seems like a ready solution to the problem, it has serious disadvantages: First, the process of detaching cables, switching devices, and reattaching cables is almost an impossible task for an individual with only one hand. In fact many amputees find this task so intimidating that they rely on others to do it for them. Second, the amputee must purchase and maintain two individual devices. In addition, the amputee does not have combined operating advantages readily accessible for spontaneous use as needed.

SUMMARY OF THE INVENTION

To overcome these obstacles, the present invention combines the functions and advantages of a split hook and a hand into a single device. By replacing the index and middle finger of a hand unit with a hook and covering the hook portion with material shaped in the form of fingers, the cosmetic appeal of a hand is retained. The combination of a hand and hook is economical in that it obviates the purchase of separate hook and hand units. In addition, such a combination eliminates the need to change back and forth between hook and hand, a process that is almost impossible for many amputees.

The construction of the present invention is straight forward—essentially the index and middle finger of a mechanical hand being replaced by an operable split hook. A portion of the shell of the hand is removed to allow for the operating lever of the hook to extend through the side of the shell. The two sections of the split hook are covered with a suitable material which is shaped in the form of fingers. The extreme terminal portion and contacting sides of the two sections of the split hook are left exposed so that no impairment of hook function occurs. The hook is operated by a cabling means attached to the forearm or shoulder.

In addition to a functional hook, the present invention is also equipped with an operable thumb which is attached to the shell by means of a pivot pin. A ratchet bar is secured to the base of the shell. A pawl is attached to the base of the thumb and engages the ratchet bar thus locking the thumb in a desired position. The thumb can be released by upward pressure on a lever that protrudes through the side of the shell thereby releasing the pawl from the ratchet. The movable locking thumb allows the amputee to hold a soft object between the thumb and the hook without crushing it and also allows the amputee to hold an object for an extended period of time without having to apply constant control cable tension. Nonoperable third and little fingers are attached to the shell of the hand to allow for greater stability in holding objects using the thumb and for cosmetic appearance.

In essence, this invention combines the dual functions of a split hook and a conventional mechanical hand into a single unit obviating the complex and difficult process of interchanging hook and hand units while at the same time providing the dexterity of a hook and the advantages of an operable thumb including extended holding times without the need of cable tension. Covering the split hook sections with finger-like material and covering the hand with a cosmetic glove gives the invention the cosmetic appeal of a natural hand.

BRIEF DESCRIPTION OF THE DRAWINGS

FIG. is a posterior view of the hand prosthesis.

FIG. 2 is a side view of the hand prosthesis showing the movable thumb in a grasping position.

FIG. 3 is an enlarged sectional view taken substantially as indicated by line 3—3 in FIG. 1.

Figure 4:
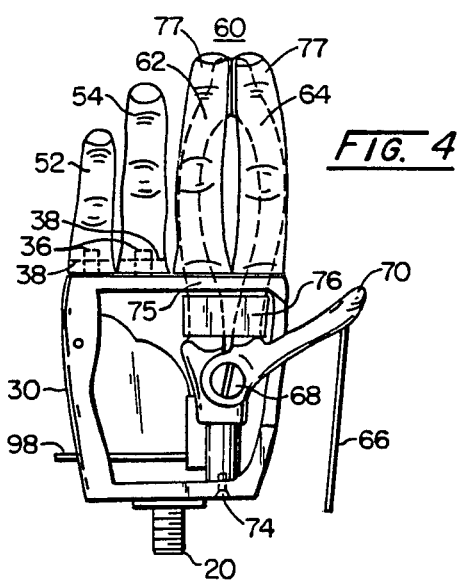
FIG. 4 is a posterior view of the prosthesis with the posterior and anterior covering removed and showing the mechanism of the split hook.

It may be possible that shapes other than those of FIGS. 1-7 could be used, but that which is shown is preferred and typical.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents that operate in a similar manner to accomplish a similar purpose. Although a preferred embodiment of the invention has been herein described, it will be understood that various changes and modifications in the illustrated and described structure can be affected without departure from the basic principles that underlay the invention. Changes and modifications of this type are therefore deemed to be circumscribed by the spirit and scope of the invention, except as the same may be necessarily modified by the appended claims or reasonable equivalence thereof.

DETAILED DESCRIPTION OF THE INVENTION AND BEST MODE FOR CARRYING OUT THE PREFERRED EMBODIMENT

The present invention relates to prosthetic devices that replace a missing hand, either partially or completely. More particularly, this prosthesis satisfies the needs of malformed and injured persons who do not have complete hands or no hand at all. It is to be understood at the outset that malformations and injuries vary greatly and that all or any portion of the prothesis herein disclosed is to be employed as circumstances require. As shown, the person affected is an amputee who has lost his entire hand and portion of the arm above the styloid process of the radius and ulna. Consequently, it is the entire wrist and hand which is to be replaced and secured to the remaining portion of the radius and ulna. Thus, typically there is a socket 10 that fits to the amputees arm 12 over a secure portion thereof. The interior configuration of the socket conforms to the flesh that surrounds the person's arm portion and all of which is molded to fit reasonably snug therein. The socket end portion terminates at an end face normal to the axis of the socket. Typically the transverse cross-section at the end of the socket contains a threaded receptacle 14 capable of receiving a threaded fastener 20 attached to the prosthetic hand and securing the hand to the transverse section of the socket.

As shown in FIG. 1 the hand prosthesis consists of a hand frame shell 30 which replaces the carpel bone section of the amputee's hand. The hand frame shell 30 is generally planar or flat across the back of the hand frame shell, i.e. the dorsal portion of the hand frame shell 30 as shown in FIG. 1 and the rightward portion of the hand frame shell 30 as viewed in FIG. 3. A threaded fastener 20 projects from the rear face of the hand frame shell 30 to mount the shell to the receptacle found in the socket 10. As shown in FIG. 4, formed little finger 52 and third finger 54 extend from the front of the hand frame shell 30 and are joined to the shell by a suitable nub 36 and pin 38 arrangement. Split hook members 62 and 64 also extend forward from the hand frame shell as part of the split hook 60. A cable 66 allows for lateral movement of hook members 62 and 64 in the plane of the hand frame shell 30.

As shown in FIG. 2, thumb 56 extends on a bias from the interior portion of the hand frame shell 30. The thumb 56 is joined to the hand frame shell 30 by a pivot pin 58 thereby providing thumb movement in a plane that is generally perpendicular to the lateral operational plane of the hand and generally passing between the split hook members, so as to enable cooperation between the thumb 56 and hook members 62 and 64 to give a holding ability.

As shown in FIG. 4, the split hook 60 consists of a stationary hook member 62, a second movable hook member 64, a pivot pin 68, and a hook lever 70 for opening movable hook member 64. Such opening is accomplished by a cable attached to the forearm or shoulder (not shown) of the amputee and extending and fastened to hook lever 70. The hook 60 is secured in the hand frame shell 30 by a screw 74 through the rear of the hand frame shell 30 and a set screw 75 through the front of the hand frame shell 30. The split hook members 62 and 64 are maintained in a closed position by means of one or more rubber bands 76 secured around the hook members 62 and 64. The hook members 62 and 64 are covered with suitable material such as epoxy resin shaped in the form of fingers 77. The interior terminal portion and tips of hook members 62 and 64 are left free of covering material 77 so as to retain their functionality.

Figure 5:
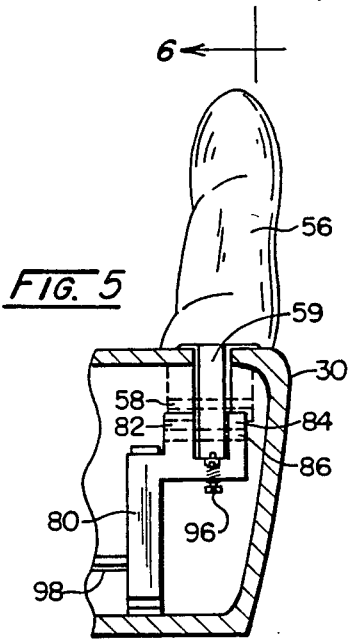
FIG. 5 is a cross-sectional posterior view taken substantially as indicated by line 5—5 in FIG. 2 and showing the thumb locking mechanism.
Figure 6:
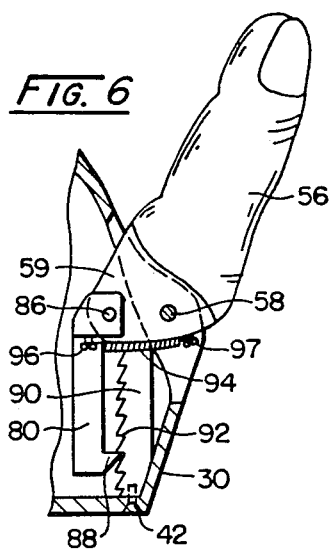
FIG. 6 is a cross-sectional side view taken substantially as indicated by line 6—6 in FIG. 5 and showing the bar ratchet and pawl assembly of the thumb locking mechanism.

As shown in FIG. 5, the thumb tang 60 is secured to the hand frame shell 30 by means of a thumb pivot pin 58. The thumb tang movably fits between legs 82 and 84 of pawl 80 and is secured thereto by means of a pivot pin 86. As shown in FIGS. 3 and 6, the pawl tooth 88 engages teeth 92 of the bar ratchet 90 which is secured to the hand frame shell 30 by means of suitable fasteners 42 and 44. The pawl 80 is maintained in engagement with the bar ratchet by means of a spring 94 that is stretched between a post 96 on the interior side of pawl 80 and a post 97 on the thumb tang 59. The pawl 80 may be disengaged from the bar ratchet 90 by upward pressure on release rod 98.

Figure 7:
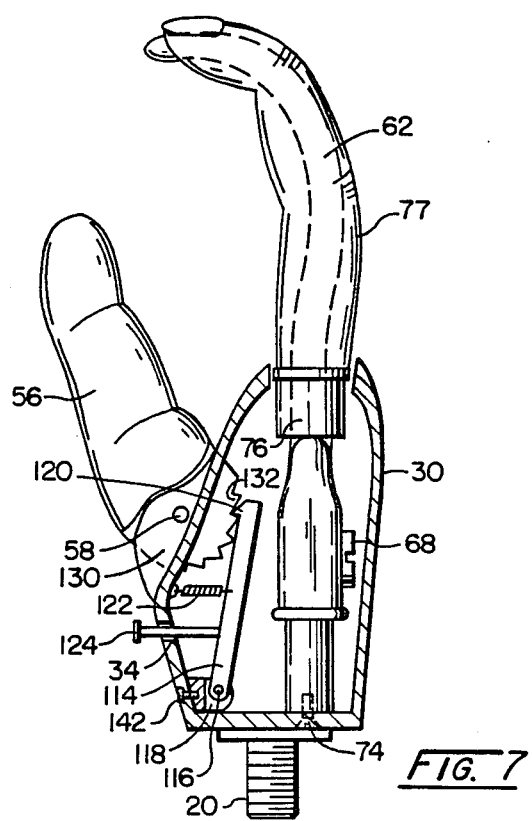
FIG. 7 is a cross-sectional side view of an alternative thumb locking mechanism.

In another version of the locking thumb shown in FIG. 7, the thumb tang 130 is formed in the shape of a wheel ratchet with ratchet teeth 132 which are coaxial with the thumb pivot pin 58. A pawl 114 pivots on pivot pin 116 which also fastens the pawl 114 to bracket 118 which is secured to the frame shell 30 by a suitable fastener 142. The opposite end of pawl 114 contains a tooth 120 that engages the teeth 132 of the thumb tang 130. Engagement of the pawl tooth 120 with the thumb tang ratchet teeth 132 is maintained by means of a spring 122 stretched between the pawl 114 and the hand frame shell 30. A release post 124 is attached to the pawl 114 and extends through a circular opening 34 in the hand frame shell 30. By pushing upward on the release post 124, the pawl tooth 120 is released from the thumb base ratchet teeth allowing the thumb 56 to freely pivot about pivot pin 58.

In operation, the split hook member 64 is moved in a lateral direction by cable 66 which is appropriately connected to the forearm or shoulder of the amputee. In this mode of operation, the amputee has all of the manipulative advantages associated with the classic split hook, especially the ability to grasp and handle small objects. By using the moveable thumb 56 in cooperation with the rigid hook members, the amputee is able to acquire prehensile function to hold larger objects as illustrated in FIG. 2. The thumb requires no cable manipulation and, because of its lockable feature, enables the amputee to hold objects for long periods of time.

It may be possible that changes in the configurations to other than those shown could be used but that which is shown is preferred and typical. It is to be especially noted that the invention is illustrated for the left hand. A right hand is assembled in the reverse order. Moreover it is to be understood that the anatomy to be replaced varies widely according to the deformation and injury sustained and that the invention may be modified to accommodate those portions of the anatomy that have been lost.

Without departing from the spirit of this invention, various means of fastening the material together may be used. It is therefore understood that although the present invention has been specifically disclosed with the preferred embodiment and examples, modifications to the design concerning design and shape may be apparent to those skilled in the art, and such modifications and variations are considered to be within the scope of the invention and the appended claims.

I claim:

1. A hand prosthesis that integrates an amputee operated split hook into hand with an independently operable lockable thumb thereby making the split hook and the lockable thumb simultaneously available to an amputee and allows the amputee to selectively use the split hook for handling objects requiring pinch pressure or to use the lockable thumb in cooperation with the split hook for grasping objects requiring a prehensile grip comprising:
   a. a hand frame shell that is generally planar across the dorsal portion and that serves in place of an amputee's hand carpel bone section;
   b. a split hook attached to said hand frame shell and having a stationary hook member and a movable hook member generally laterally operable is a plane of said generally dorsal planar head frame shell so as to provide a pinch pressure;
   c. means attached to said moveable hook member for selectively operating said movable hook member;
   d. a thumb
      1. movably attached at a first end of said thumb to said hand frame shell,
      2. generally moveable in a plane essentially perpendicular to said lateral operational plane of said split hook and passing between said stationary and movable hook member, and
      3. cooperating with said split hook so as to provide a prehensile grip;
   e. means attached to said thumb for selectively locking and unlocking said thumb in an amputee selected position wherein said thumb locking and unlocking means and said hook operating means are simultaneously available to provide an amputee with an immediate selection of either nook pinch pressure or a thumb-hook prehensile grip.

2. The hand prosthesis of claim 1 wherein said movable thumb is attached to said hand frame shell by a pivot pin.

3. The hand prosthesis or claim 1 wherein said means for operating said moveable split hook member is a control cable and at least one rubber band.

4. The hand prosthesis or claim 1 further comprising at least one additional finger attached to said hand frame shell.

5. The hand prosthesis of claim 1 with each hook member of said split hook having a solid finger-shaped covering securely attached to it.

6. The hand prosthesis or claim 2 wherein said means for locking and unlocking said thumb is a ratchet and pawl assembly.

7. The hand prosthesis of claim 6 with said ratchet and pawl assembly further comprising:
   a. a ratchet rigidly affixed to said hand frame shell,
   b. a pawl pivotally attached to said first end of said thumb, and
   c. means for engaging said pawl with said ratchet.

8. The hand prosthesis or claim 7 wherein said means for engaging said pawl with said ratchet is a spring.

9. The hand prosthesis or claim 8 further comprising means for disengaging said ratchet and pawl assembly.

10. The hand prosthesis of claim 9 wherein said means for disengaging said ratchet and pawl assembly is a release post attached to said pawl.

11. The hand prosthesis of claim 8 with said ratchet and pawl assembly further comprising:
   a. a hemispherical ratchet formed as part of a tang formed at said first end of said thumb and coaxial with said pivot pin of said thumb,
   b. a pawl pivotally attached to said hand frame shell, and
   c. means for engaging said pawl with said ratchet.

12. The hand prosthesis of claim 11 wherein said means for engaging said pawl with said ratchet is spring.

13. The hand prosthesis of claim 12 further comprising a pawl and ratchet disengaging means.

14. The hand prosthesis of claim 13 wherein said ratchet and pawl disengaging means is a post
   a. attached to said pawl between a point where said pawl is pivotally attached to said hand frame shell and a point where said pawl engages said ratchet, and
   b. extending through said hand frame shell.

* * * * *